United States Patent [19]

Baillie et al.

[11] 4,399,287

[45] Aug. 16, 1983

[54] PHOSPHINIC ACID DERIVATIVES

[75] Inventors: Alister C. Baillie, Bottisham; Brian J. Wright, Bishops Stortford; Kenneth Wright, Lode; Christopher G. Earnshaw, Chesterton, all of England

[73] Assignee: FBC Limited, Hauxton, England

[21] Appl. No.: 213,602

[22] Filed: Dec. 5, 1980

[30] Foreign Application Priority Data

Dec. 8, 1979 [GB] United Kingdom ............. 79/42420

[51] Int. Cl.³ .................. C07F 9/30; A01N 57/20; A01N 57/24
[52] U.S. Cl. .................. 548/119; 260/455 P; 260/465.4; 260/501.21; 260/502.4 R; 260/502.5 G; 260/941; 260/968; 71/86; 71/87; 424/199; 424/200; 560/179
[58] Field of Search ............ 260/501.21, 502.4 R, 260/502.5 G, 941, 465.4; 548/119

[56] References Cited

FOREIGN PATENT DOCUMENTS 9348 4/1980 European Pat. Off. ............ 260/941

OTHER PUBLICATIONS

Ivanov et al., "Chemical Abstracts", vol. 61, (1964) 12030e.

Primary Examiner—Anton H. Sutto
Attorney, Agent, or Firm—Morgan, Finnegan, Pine, Foley & Lee

[57] ABSTRACT

There are described compounds of the formula I,

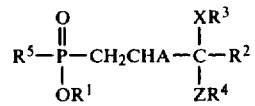

in which
$R^5$ is methyl or halomethyl,
$R^2$ is —CN, —CONRyRz, —COOR⁶ or —COSR⁶,
$R^1$ and $R^6$ each represent hydrogen, a cation or an optionally substituted alkyl, alkenyl, alkynyl or aryl,
Ry and Rz each represent hydrogen, alkyl or aryl,
A represents hydrogen, or
A and one of —XR³ and —ZR⁴ together form a double bond, and the other of —XR³ and —ZR⁴ represents —OR¹⁰ or —NHR¹¹ in which R¹⁰ is alkyl or acyl and R¹¹ is alkyl, aryl or acyl,
X and Z (when not forming part of a double bond with A), which may be the same or different, each represent oxygen, sulphur or a group —NR⁷—,
$R^7$ represents hydrogen or alkyl,
$R^3$ and $R^4$ each represent alkyl or $R^3$ and $R^4$ together form an optionally substituted alkylene or arylene chain
or —XR³ and —ZR⁴ together form =C(CN)₂ or =NR⁸, in which R⁸ represents alkoxy, benzyloxy, hydroxy, phenyl, —NHCONH₂, —NHCSNH₂ or —NH phenyl,
or one of —XR³ and —ZR⁴ is —OH (or an ester or ether thereof) and the other, is hydrogen, —CN or —SO₃⁻ cation,
or —XR³ and —ZR⁴ together form carbonyl oxygen.

There are also described methods for making the compounds and heribicidal compositions containing them.

7 Claims, No Drawings

PHOSPHINIC ACID DERIVATIVES

This invention concerns pesticidal and in particular herbicidal compositions, new pesticidally active compounds, and processes for the preparation of such compounds.

In one aspect, this invention provides a pesticidal composition comprising one or more compounds of the formula I,

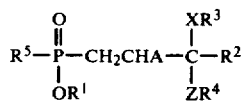

in which $R^5$ is methyl or halomethyl, $R^2$ is —CN, —CONRyRz, —COOR$^6$ or —COSR$^6$, $R^1$ and $R^6$, which may be the same or different, each represent hydrogen, a cation, alkyl, alkenyl, alkynyl or aryl; the aryl optionally being substituted by one or more of halogen, alkoxy, nitro, alkyl, —CF$_3$, —CN or —COOH or a salt, ester or amide thereof; and the alkyl, alkenyl and alkynyl optionally being substituted by one or more of —CN, halogen, alkoxy or aryl, Ry and Rz, which may be the same or different, each represent hydrogen, alkyl or aryl, A represents hydrogen, or A and one of —XR$^3$ and —ZR$^4$ together form a double bond, and the other of —XR$^3$ and —ZR$^4$ represents —OR$^{10}$ or —NHR$^{11}$ in which R$^{10}$ is alkyl or acyl and R$^{11}$ is alkyl, aryl or acyl, X and Z (when not forming part of a double bond with A), which may be the same or different, each represent oxygen, sulphur or a group —NR$^7$—, R$^7$ represents hydrogen or alkyl, R$^3$ and R$^4$, which may be the same or different, each represent alkyl; or R$^3$ and R$^4$ together form an alkylene or arylene chain, each of which chains may optionally be substituted by hydroxy, alkoxy, alkyl, halogen, carbonyl oxygen or alkoxycarbonyl, or —XR$^3$ and —ZR$^4$ together form =C(CN)$_2$ or =NR$^8$, in which R$^8$ represents alkoxy, benzyloxy, hydroxy, phenyl, —NHCONH$_2$, —NHCSNH$_2$ or —NH phenyl in which the phenyl is optionally substituted by one or more nitro groups, or one of —XR$^3$ and —ZR$^4$ is —OH (or an ester or ether thereof) and the other, is hydrogen, —CN or —SO$_3^\ominus$ cation, or —XR$^3$ and —ZR$^4$ together form carbonyl oxygen.

In another aspect this invention provides a method of combating or dessicating plants, at a locus either infested with weeds or liable to infestation therewith or a locus at which there are plants, which method comprises applying to the locus an effective amount of one or more compounds of formula I.

According to the invention we also provide the compounds of formula I as new compounds.

When R$^2$ is a group —CONRyRz, Ry and Rz, when they contain carbon, may independently contain up to and including 7 carbon atoms and may be, for example, ethyl or phenyl. We prefer R$^2$ to be —CN only when —XR$^3$ is hydrogen and —ZR$^4$ is —OH or an ester or ether thereof.

When R$^1$ or R$^6$ represents or contains a cation, or when —XR$^3$ or —ZR$^4$ represents —SO$_3^\ominus$ cation, the cation may be a tri-, or preferably a di- or mono-valent cation. We prefer the cation to be an alkali metal (e.g. sodium or potassium), an alkaline earth metal (e.g. magnesium or calcium), or the ammonium (NH$_4^\oplus$) cation or a protonated primary-, secondary- or tertiary-amine (e.g. a primary-, secondary- or tertiary-cycloalkyl- or alkyl- or phenyl-amine in which each alkyl group contains 1 to 16 carbon atoms) or a quaternary (e.g. a quaternary alkyl C 1 to 16) ammonium cation. The cation may also be a herbicidally active cation, e.g. the cation of paraquat, difenzoquat or a triazolium compound such as is disclosed in Belgian Patent Specification No. 848,615.

When R$^1$ or R$^6$ are optionally substituted alkyl, alkenyl or alkynyl they preferably contain up to 10, more preferably up to 6 and most preferably up to and including 3 carbon atoms. Thus R$^1$ or R$^6$ may be, for example, ethyl or isopropyl. When R$^1$ or R$^6$ themselves carry a substituent that substituent preferably contains up to 6 carbon atoms. When R$^1$ or R$^6$ is, or contains, an aryl group we prefer it to be a phenyl group.

When R$^1$ or R$^6$ represent a group substituted by a —COOH group, the —COOH group may be in the form of an agriculturally acceptable salt, ester or amide thereof. Suitable salts include those having a cation as described above. Suitable esters include C 1 to 10 esters, e.g. C 1 to 10 alkyl esters, and suitable amides include those derived from ammonia or from a mono- or dialkyl or aryl-, (e.g. phenyl-) amine.

We prefer —XR$^3$ and —ZR$^4$, when they are separate, each to contain up to and including 10, and preferably up to and including 6 carbon atoms. When R$^3$ and R$^4$ together form an optionally substituted alkylene or arylene chain we prefer the combined R$^3$ and R$^4$ group to contain up to and including 8 and more preferably 2, 3 or 4 carbon atoms. Thus R$^3$ and R$^4$ may together form a propylene, ethylene, 1,2-dimethylethylene or an o-phenylene chain. We prefer R$^7$ to be hydrogen or to contain up to 10, and preferably up to 6 carbon atoms. When R$^8$ is alkoxy it preferably contains 1 to 6 carbon atoms. When —XR$^3$ is an ester of an —OH group we prefer R$^3$ to be alkanoyl C 2 to 6. When R$^{10}$ or R$^{11}$ is acyl we prefer it to be alkanoyl C 2 to 6, and when R$^{11}$ is aryl we prefer it to be phenyl.

As a specific group of compounds of formula I we provide compounds in which R$^5$ is methyl; R$^2$ is —CONRaRb in which Ra and Rb independently represent hydrogen or alkyl C 1 to 6, e.g. ethyl, or R$^2$ is —COOR$^6$ in which R$^6$ is hydrogen, a cation, alkenyl C 2 to 6, benzyl, or alkyl C 1 to 6 optionally substituted by —CN; R$^1$ is hydrogen, a cation or alkyl C 1 to 6 optionally substituted by —CN; —XR$^3$ and —ZR$^4$ together form carbonyl oxygen, =N—NHCONH$_2$, =N—NHCSNH$_2$, =N—NH(2,4-dinitrophenyl), =NOH or a chain —SCH$_2$CH$_2$NH—, or represent the pairs of groups (alkoxy C 1 to 6)$_2$, (alkythio C 1 to 6)$_2$, —OH and —CN, or —OH and —SO$_3^\ominus$; or A and one of —XR$^3$ and —ZR$^4$ together form a double bond and the other of —XR$^3$ and —ZR$^4$ represents —O—alkanoyl C 2 to 6,—NH—alkanoyl C 2 to 6 or —NH-phenyl.

The preferred compounds are those of Examples 1, 4 and 16.

According to the invention we also provide a process for the production of a compound of formula I, which comprises (a) production of a compound of formula I in which A is hydrogen and —XR³ and —ZR⁴ together form carbonyl oxygen, by (i) selective decarboxylation of a compound of formula II,

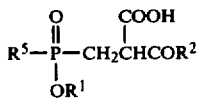

in which R¹, R² and R⁵ are as defined above, or (ii) selective oxidation of a compound of formula III,

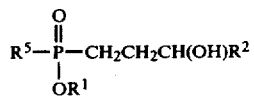

in which R¹, R² and R⁵ are as defined above, (b) production of a compound of formula I in which —XR³ is hydrogen, —ZR⁴ is hydroxy and R² is —CN, by reaction of a compound of formula IV,

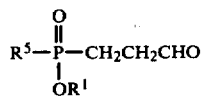

in which R¹ and R⁵ are as defined above, with hydrocyanic acid, or a cyanide, (c) production of a compound of formula I in which A is hydrogen and —XR³ and —ZR⁴ together form =N—OH, which comprises reacting a compound of formula V,

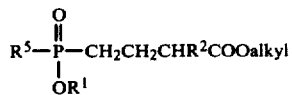

in which R¹, R² and R⁵ are as defined above, with an organic nitrite, (d) conversion of a compound of formula I in which R¹ and R⁶ are cations, to a corresponding compound of formula I in which R¹ and R⁶ are other than hydrogen or a cation, (e) production of a compound of formula I in which R⁶ is other than hydrogen or a cation by esterification of a corresponding compound of formula I in which R⁶ is hydrogen or a cation, (f) production of a compound of formula I in which one or both of R¹ and R⁶ is a cation or in which —ZR⁴ is a group —SO₃⊖ cation, which comprises reaction of a corresponding compound of formula I in which at least one of R¹ and R⁶ is other than a cation or is another cation, or —ZR⁴ is a group —SO₃R″ in which R″ is hydrogen or another cation, with a compound containing the desired cation in available form, (g) production of a compound of formula I in which —XR³ and —ZR⁴ do not together form carbonyl oxygen by reacting a compound of formula I in which —XR³ and —ZR⁴ together form carbonyl oxygen with an appropriate reagent, (h) production of a compound of formula I in which R² is —CONRyRz by reaction of a corresponding compound of formula I in which R² is —COOR⁶ with ammonia or an amine RyNHRz, or (i) production of a compound of formula I in which —XR³ and —ZR⁴ are both —S alkyl, by reaction of a compound of formula VII,

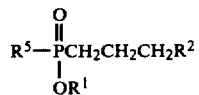

in which R¹, R² and R⁵ are as defined above, with an alkyl aryl disulphide under basic conditions.

The reaction of process (a) (i) is preferably carried out in a solvent which is inert under the reaction conditions, e.g. an aqueous medium. The reaction is preferably carried out at an elevated temperature, e.g. of from 40° to 150° C. and especially at the reflux temperature of the solvent. The reaction of process (a) (i) may be carried out using the compound of formula II itself or a suitable derivative, e.g. an ester, thereof which is converted, e.g. by hydrolysis, to the compound of formula II under the reaction conditions. The ester may be of a carboxylic acid group R² and/or of the phosphinyl group. When an ester of formula II is used the reaction may be carried out under basic, or preferably acidic conditions, e.g. in refluxing aqueous HCl.

The reaction of process (a) (ii) may be carried out by using conventional oxidising conditions, e.g. by use of potassium permanganate, chromium trioxide, a dichromate or a chlorochromate anion.

Process (b) may be carried out under conditions conventional for the production of cyanohydrins, e.g. by use of sodium or potassium cyanide in an aqueous medium at a pH of about 4 or 5 at a temperature of from about 10° to 50° C.

In process (c) the organic nitrite may be a lower alkyl nitrite, e.g. ethyl nitrite. The reaction is preferably carried out under strongly basic conditions and in a solvent which is inert under the reaction conditions, e.g. ethanol. The reaction is preferably carried out at less than room temperature, e.g. at from −10° to 0° C.

In process (d) the conversion may be carried out by reaction with a compound $R^{1a}Y$ in which $R^{1a}$ has the same significances as R¹ save that $R^{1a}$ cannot represent hydrogen or a cation, and Y represents a good leaving group. The good leaving group Y may be an anion forming group, e.g. a bromine atom or an alkane- or p-toluene sulphonate group. The reaction is preferably carried out in a solvent which is inert under the reaction conditions, e.g. acetonitrile. The reaction may be carried out at an elevated temperature, e.g. of from 60° to 100° C.

Process (e) may be carried out under conventional esterification conditions, e.g. reaction of the free acid of formula I with an appropriate alcohol, e.g. a C 1 to 6 alkanol, in the presence of a catalytic amount of an acid, e.g. p-toluene sulphonic acid, if desired with simultaneous removal of the water. The reaction is preferably carried out at an elevated temperature, e.g. of from 80° to 110° C. and preferably at the reflux temperature of the reaction mixture.

In process (f) the free acid, or an ester thereof, may be converted to the desired salt, or one salt may be converted to another by a metathetical step. Compounds containing the desired cation in available form include bases and ion exchange resins. In general we prefer to form the salt by treating the free acid of formula I, or an ester thereof, with an appropriate base.

Process (g) may comprise reaction of a compound of formula I in which —XR$^3$ and —ZR$^4$ together form carbonyl oxygen with an appropriate alcohol, (for example at an elevated temperature, e.g. at reflux in the presence of a molecular sieve), an amine (for example aniline in an inert solvent such as benzene, at an elevated temperature, e.g. reflux, with removal of water) malononitrile (for example in ethanol at ambient temperature) an alkoxyamine (for example in an inert solvent, e.g. aqueous ethanol) an aralkyloxy-amine, e.g. benzyloxyamine (for example in aqueous ethanol)hydroxylamine (for example in aqueous ethanol) an optionally substituted phenylhydrazine such as dinitrophenylhydrazine (for example at reflux in a solvent which is inert under the reaction conditions, e.g. ethanol), semicarbazide (for example by reaction in water at ambient temperature), thiosemicarbazide (for example by reaction in water at ambient temperature), a cyanide (for example in water at ambient temperature at a pH of about 6) or with sulphur dioxide in the presence of base. This process may also involve production of a derivative of an enolic or enamino form of a compound of formula I (i.e. a compound in which A and one of XR$^3$ and ZR$^4$ together form a double bond). Thus for example the compound of formula I in which XR$^3$ and XR$^4$ together form carbonyl oxygen may be reacted with an appropriate alkanoic acid anhydride or amide, or an aryl amine, e.g. at an elevated temperature. The conversions may be carried out under conditions, and using reagents, which are conventional for the conversion of carbonyl oxygen to the appropriate enolic or enamino derivative.

Process (h) may be carried out in a suitable solvent, e.g. a lower alkanol such as isopropanol, and at a temperature of from about 20° to 120° C.

Process (i) may be carried out in a suitable solvent, e.g. tetrahydrofuran, in the presence of a strong base, e.g. sodium hydride. The alkyl aryl disulphide may be, for example o-nitrophenyl ethyl disulphide, and the reaction may be carried out at a temperature of from 50° to 150° C., conveniently at the reflux temperature of the solvent.

Compounds of formula II, and particularly the esters thereof, may be made from known compounds using techniques known per se, e.g. by reaction of a compound of formula VI,

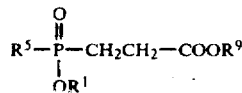

in which R$^1$ and R$^5$ are as defined above, and R$^9$ is alkyl, e.g. C 1 to 6 alkyl, with a dialkyl oxalate, e.g. diethyl oxalate, followed by hydrolysis.

The compounds of formula II (and the esters thereof) are new and the invention also provides these compounds per se. Compounds of formula II in which R$^2$ is other than a —COOR$^6$ group may be made by conventional techniques from compounds of formula II in which R$^2$ is —COOR$^6$ or by a process analogous to that described above, but in which the compound of formula VI is reacted with a compound alkylOOCCONRyRz or alkylOOCCN. One group R$^2$ may, if desired, be converted to another.

Compounds of formula IV, V, VI and VII are either known or may be made from known compounds using techniques known per se.

Compounds of formula III form a group of compounds of formula I.

The compounds and compositions of the invention possess herbicidal and/or plant growth regulant or retardant activity, especially when employed post-emergence. The compounds also have desiccant properties and are therefore useful in treating the haulms of legumes, e.g. peas, soya beans and potatoes, and in the defoliation of cotton. They are also useful in the post-harvest control of weeds in the stubble of wheat and barley.

The compounds and compositions of the invention are also of use for total weed control, e.g. on railway tracks, and for directed spray application to high standing crops such as growing cotton, maize, tobacco, sugar cane, orchards, vineyards, in rubber, cocoa, tea, coffee or palm plantations and in forestry.

Certain of the compounds are selective herbicides and may be used for the selective control of weeds in crops.

The compounds of formula I are preferably employed in the form of a composition containing a carrier and/or a surface active agent.

The compositions may be prepared by admixing the ingredients.

Those compounds soluble in water may be used as aqueous solutions with or without a surface active agent.

If desired the compositions may be produced initially in the form of concentrates, e.g. containing 0.5-85% of the present compounds, and these are diluted with water or a hydrocarbon, usually water, for application, generally such that the concentration of the compounds is 0.05-5%, percentages and parts in this specification being by weight unless otherwise indicated.

The carrier may be a liquid, for example water (e.g. water used to dilute a concentrate for application). If water is employed as carrier in a concentrate, an organic solvent may also be present as carrier, though this is not usually employed. A surface active agent may advantageously be present.

The carrier may be a liquid other than water, for example an organic solvent, such as a water immiscible solvent, e.g. a hydrocarbon which boils within the range 130°-270° C., in which the compound is dissolved or suspended. A concentrate containing a water immiscible solvent suitably also contains a surface active agent so that the concentrate acts as a self-emulsifiable oil on admixture with water. The liquid may be a water-miscible solvent, e.g. 2-methoxy ethanol, methanol, propylene glycol, ethylene glycol, diethylene glycol, diethylene glycol monoethyl ether, formamide or methylformamide.

The carrier may be a solid, which may be finely divided. Examples of suitably solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the compound in particulate form with a particulate carrier, or by spraying molten compound on to the particulate carrier, admixing a wetting agent and a dispersing agent and finely grinding the whole powder mixture.

An aerosol composition may be formed by admixing the compound with a propellent, e.g. a polyhalogenated alkane such as dichlorodifluoromethane, and suitably also with a solvent.

A flowable suspension concentrate may be formed by grinding substantially water insoluble compounds with water, a wetting agent and a suspending agent.

Thus the present composition can for example be solid (e.g. dust or granules) and contain a solid carrier, or liquid (e.g. an emulsifiable concentrate) and contain a liquid carrier which is a hydrocarbon which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example soaps, mono- or diesters of phosphoric acid with fatty alcohol ethoxylates or salts of such esters, fatty alcohol sulphates such as sodium dodecyl sulphate, sodium octadecyl sulphate or sodium cetyl sulphate, ethoxylated fatty alcohol sulphates, ethoxylated alkylphenol sulphates, lignin sulphonates, petroleum sulphonates, alkyl-aryl sulphonates such as alkyl-benzene sulphonates or lower alkylnaphthalene sulphonates, e.g. butylnaphthalene sulphonate, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates, e.g. the sodium sulphonate of dioctyl succinate. Ionic surface active agents may tend to result in precipitation if employed in some formulations with certain of the compounds of the invention. Any surface active agent should of course be so chosen as to avoid precipitation.

The surface active agents may also comprise non-ionic agents, for example, condensation products of fatty acid esters, fatty alcohols, fatty acid amides or fatty-, alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, dialkyl sulphosuccinates, alkyl phenol ethoxylates, and fatty alkyl ethoxylates.

Higher quantities of surface active agent, e.g. 5–50% of concentrate, than is normally present in commercial pesticidal or plant growth requlant compositions tend to increase considerably the activity of the present compounds.

The surface active agent employed to produce this potentiating effect may be selected from those described above. It is preferably a non-ionic surface active agent, especially an alkyl-substituted phenol condensed with ethylene oxide, e.g. tributylphenol condensed with 11 moles of ethylene oxide (available under the trade mark Sapogenat T110). The potentiating surface active agent may be admixed with the present compound for instance at the point of use, e.g. in a spray tank, or before, e.g. in a concentrate. Preferably the amount of potentiating surface active agent applied in a spray of the present compound is 0.1–5% especially 1%.

The present active compound may be admixed with another pesticide, e.g. herbicide, insecticide or fungicide, or with a plant growth regulant. The invention provides a one pack presentation, in which the present compound is already mixed with another pesticide or plant growth regulant, and also a single package designed to hold the present compound and other pesticide or the plant growth regulant in separate containers, for mixing, e.g. in a spray tank, for application. Particular advantages are obtained with mixtures with another pesticide. The present compound may be used sequentially with another pesticide or plant growth regulant particularly with another fungicide or herbicide.

The herbicide may be for example one or more of a phenoxyaliphatic acid, substituted urea, triazine, phenol, nitrile, bipyridylium compound, substituted benzoic acid, halogenated aliphatic acid, carbamate, thiocarbamate, chloroacetamide, diazine, benzofuran or arsenic herbicide. In respect of selective herbicidal compositions for post-emergence use, the present compound may be used in admixture with, for example, a substituted phenoxyaliphatic acid; in respect of selective herbicidal compositions for pre-emergence use, the present compound may be used in admixture with, for example, a substituted urea, triazine, S-2,3-dichloroallyl di-isopropylthiocarbamate or S-2,3-trichloroallyl di-isopropylthiocarbamate.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples of the substituted phenoxyaliphatic acids which may be mentioned include 2,4-dichlorophenoxyacetic acid, 2-(2,4-dichlorophenoxy)propionic acid, 2-methyl-4-chlorophenoxyacetic acid, 2,4,5-trichlorophenoxyacetic acid, gamma-2,4-dichlorophenoxybutyric acid, gamma-b 2-methyl-4-chlorophenoxybutyric acid, alpha-2-methyl-4-chlorophenoxypropionic acid, 2-(4-[2,4-dichlorophenoxy]phenoxy)propionic acid and 2-(4-[4-chlorophenoxy]phenoxy)propionic acid.

The substituted urea generally comprises a di-, tri- or tetra-substituted urea such as N'-(3-chloro-4-methoxyphenyl)-N,N-dimethylurea, N'-(3-chloro-4-methylphenyl)-N,N-dimethylurea, N'-parachlorophenyl-N,N-dimethylurea, N-butyl-N'-(3,4-dichlorophenyl)-N-methylurea, N'-parachlorophenyl-O,N,N,-trimethylisourea, N'-p-chlorophenyl-N-methoxy-N-methylurea, N,N-dimethyl-N'-phenylurea, 3-(4-bromophenyl)-1-methoxy-1-methylurea, 1-(2-benzothiazolyl)-3-methylurea, N,N,-dimethyl-N'-(4-[1-methylethyl]-phenyl)urea, N'-(3,4-dichlorophenyl)-N-methoxy-N-methylurea, N,N-dimethyl-N'-[3-(trifluoromethyl)-phenyl]urea, N'-(3,4-dichlorophenyl)-N,N-dimethylurea or N'-(3-(1,1,2,2-tetrafluoroethoxy)phenyl)-N,N-dimethylurea.

The triazine herbicide generally comprises 2-chloro-4-(1-cyano-1-methylamino)-6-ethylamino-1,3,5-triazine or 2-isopropylamino-4-(3-methoxypropylamino)-6-methylthio-1,3,5-triazine or a compound of the formula:

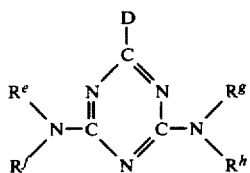

where D is halogen, alkoxy or alkylthio, R$^e$ and R$^g$ are the same or different and are hydrogen or alkyl and R$^f$ and R$^h$ are the same or different alkyl groups, such as 2-chloro-4,6-bisethylamino-1,3,5-triazine, 2-chloro-4-ethylamino-6-diethylamino-1,3,5-triazine, 2-chloro-6-ethylamino-4-isopropylamino-1,3,5-triazine or 2,4-bis-(isopropylamino)-6-methylthio-1,3,5-triazine.

The phenol herbicide generally comprises 4,6-dinitro-o-cresol, 4,6-dinitro-2-sec-butylphenol or pentachlorophenol. The nitrile herbicide generally comprises 3,5-diiodo-4-hydroxy-benzonitrile, 3,5-dibromo-4-hydroxybenzonitrile or 2,6-dichlorobenzonitrile. The bipyridylium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichlorobenzoic acid, 2-methoxy-3,6-dichlorobenzoic acid or N-(1,1-dimethylpropynyl)-3,5-dichlorobenzamide. The halogenated aliphatic acid herbicide generally comprises trichloroacetic acid or 2,2-dichloropropionic acid. The carbamate herbicide generally comprises isopropyl N-(3-chlorophenyl)carbamate, 4-chloro-2-butynyl N-(3-chlorophenyl)carbamate, methyl 3-(m-tolylcarbamoyloxy)phenylcarbamate, isopropyl N-(3-(N-ethyl-N-phenylcarbamoyloxy)phenyl)carbamate, or D-N-ethyl-2-(phenylcarbamoyloxy)propionamide. The thiocarbamate herbicide generally comprises S-ethyl N,N-dipropylthiocarbamate, S-ethyl N,N,-diisobutylthiocarbamate, S-(2,3-dichloroallyl) N,N-diisopropylthiocarbamate, S-ethyl N-ethyl-N-cyclohexylthiocarbamate, S-propyl butylethylthiocarbamate or S-(2,3,3-trichloroallyl) N,N-diisopropylthiocarbamate. The chloroacetamide herbicide generally comprises N,N,-diallyl-2-chloroacetamide, N-isopropyl-2-chloroacetanilide, N-chloroacetyl-N-(2,6-diethylphenyl)glycine ethyl ester, N-(2,6-diethylphenyl)-N-(methoxymethyl)-2-chloroacetamide, N-(2-ethyl-6-methylphenyl)-N-(2-methoxy-1-methylethyl)-2-chloroacetamide, N-chloroacetyl-N-(2,6or N-chloroacetyl-N-(2-methyl-6-ethylphenyl)glycine isopropyl ester. The diazine herbicide generally comprises 5-bromo-6-methyl-3-sec-butyluracil, 3-cyclohexyl-5,6-trimethyleneuracil, 5-amino-4-chloro-2-phenyl-3-pyridazinone or 1,2-dihydropyridazine-3,6-dione. The benzofuran herbicide may be, for example, ethofumesate or 2,3-dihydro-3,3-dimethyl-benzofuran-5-yl ethanesulphonate. The arsenic herbicide generally comprises a salt, e.g. the mono- or di-disodium salt of methane arsonic acid or cacodylic acid. Other herbicides which may be used include 1,2-dimethyl-3,5-diphenylpyrazolium ion, ethyl N-benzoyl-N-(3,4-dichlorophenyl)alanine, N-isobutyl-2-oxo-1-imidazolidine-carboxamide, aminotriazole, 2,3-dichloro-1,4-naphthoquinone, 4-amino-3,5,6-trichloropicolinic acid, N,N-dimethyl-2,2-diphenylacetamide, 2,6-dinitro-N,N-dipropyl-4-trifluoromethyl-aniline, N-butyl-N-ethyl-2,6-dinitro-4-trifluoromethylaniline, S,S,S-tributyl phosphorotrithioate, 2-ethoxy-2,3-dihydro-3,3-dimethyl-5-benzofuranyl methylsulphonate, 4-chloro-2-oxobenzothiazolin-3-yl acetic acid, 3-benzothiadiazinon-(4)-2,2-dioxide, 3,5-dibromo-4-hydroxybenzaldehyde, 2,4-dinitrophenyloxime, methyl 2-chloro-3-(4-chlorophenyl)propionate, 2-chloroethyl-trimethylammonium chloride, 4-methylsulphonyloxy-2-butynyl m-chlorocarbanilate, isopropyl 2-(N-benzoyl-3-chloro-4-fluoroanilino)propionate, methyl 2-(N-benzoyl-3-chloro-4-fluoroanilino)propionate, 2-chloro-N-(1,3-dioxolan-2-ylmethyl)-2',6'-dimethylacetanilide, 2-chloro-1-(3-ethoxy-4-nitrophenoxy)-4-trifluoromethylbenzene, methyl 2-(4-[2',4'-dichlorophenoxy]phenoxy)-propionate, isobutyl 2-(4-[4'-chlorophenoxy]phenoxy)-propionate, 1,1,1-trifluoro-2'-methyl-4'-(phenylsulphonyl)methane sulphonanilide, 4-chloro-5-methylamino-2-(3-trifluoromethylphenyl)-3(2H)-pyridazinone, 5-(2-chloro-4-trifluoromethylphenoxy)2-nitrobenzoic acid, 1-methyl-3-phenyl-5-(3-trifluoromethylphenyl)-4-pyridone, 4-(methylsulphonyl)-2,6-dinitro-N,N-dipropylaniline, 4-(2,4-dichlorophenoxy)-2-methoxy-1-nitrobenzene, N-(1-ethylpropyl)-3,4-dimethyl-2,6-dinitroaniline, 2', 4'-dimethyl-5'-(trifluoromethanesulphonamido)acetanilide, dimethyl 2,3,5,6-tetrachloroterephthalate, N-cyclopropylmethyl-2,6-dinitro-N-propyl-4-trifluoromethylaniline, N-(2-chloroethyl)-2,6-dinitro-N-propyl-4-trifluoromethylaniline, N$^1$,N$^1$-diethyl-2,6-dinitro-4-trifluoromethyl-m-phenylenediamine, N$^1$,N$^1$-dipropyl-2,6-dinitro-4-trifluoromethyl-m-phenylenediamine, N-sec-butyl-4-tert-butyl-2,6-dinitroaniline, 2-(3,4-dichlorophenyl)-4-methyl-1,2,4-oxadiazolidine-3,5-dione, 4-(dipropylamino)-3,5-dinitrobenzenesulphonamide, 1-(3-trifluoromethylphenyl)-3-chloro-4-chloromethyl-2-pyrrolidone, 2-(1-allyloxyaminobutylidine)-5,5-dimethyl-4-methoxycarbonylcyclohexane-1,3-dione, 2-(N-ethoxybutyrimidoyl)-5-(2-ethylthiopropyl)-3-hydroxy-2-cyclohexen-1-one, 2-(1-(2,5-dimethyl- phenyl)ethylsulphonyl)pyridine N-oxide, or N-(phosphonomethyl)-glycine.

The compounds may also be employed in association with a herbicidal antidote (a substance having the property of improving the safety of a herbicide to a crop), e.g. N,N-diallyl-2,2-dichloroacetamide, 4'-chloro-2-(hydroxyimino)acetanilide, 1,8-naphthalic anhydride, -(cyanomethoximino)-benzeneacetonitrile or 2,2-dimethyl-3-dichloroacetyloxazolidine. Although the antidote may be applied in admixture with active compound, it is preferably applied separately and especially as a treatment for crop seeds. The ratio by weight of herbicide to antidote is preferably from 1:4 to 4:1.

The present compound may be used in admixture or sequence with a fungicide. The fungicide may be for instance one or more of maneb (polymeric manganese ethylenebisdithiocarbamate), zineb (zinc ethylenebisdithiocarbamate), mancozeb (which can be regarded as a mixture of maneb and zineb), thiram (tetramethylthiuram disulphide), ditalimfos (O,O-diethyl phthalimidophosphonothioate), tridemorph (2,6-dimethyl-4-tridecylmorpholine), fluotrimazole (1-[diphenyl(3-trifluoromethylphenyl)methyl]-1,2,4-triazole), ethirimol (5-butyl-2-ethylamino-4-hydroxy-6-methylpyrimidine), triforine (1,4-di[2,2,2-trichloro-1-formamidoethyl]piperazine), pyracarbolid (3,4-dihydro-6-methylpyran-5-carboxanilide), zinebethylene thiuramdisulphide adduct, carbendazim (methyl benzimidazol-2-ylcarbamate), captafol (3a,4,7,7a-tetrahydro-N-[1,1,2,2-tetrachloroethylanesulphenyl]-phthalimide), thiophanate (1,2-di[3-ethoxycarbonyl-2-thioureido]benzene), proprineb (polymeric zinc propylenebisdithiocarbamate), oxycarboxin (2,3-dihydro-6-methyl-5-phenylcarbamoyl-1,4-oxathiin 4,4-dioxide), quintozene (pentachloronitrobenzene), benomyl (methyl 1-[butylcarbamoyl]-benzimidazol-2-ylcarbamate), triadimefon, benadanil(2-iodobenzanilide) and prochloraz.

The present compound may be used in admixture or sequence with an insecticide. The insecticide may be for instance one or more of bendiocarb, demeton-S-methyl (S-2-ethylthioethyl O,O-dimethyl phosphorothioate), dimethoate (O,O-dimethyl S-methylcarbamoylmethyl phosphorodithioate), formothion (S-[N-formyl-N-methylcarbamoylmethyl] O,O-dimethyl phosphorodithioate), oxydemeton-methyl (S-2-ethylsulphinylethyl, O,O-dimethyl phosphorothioate), pirimicarb (2-dimethylamino-5,6-dimethylpyrimidin-4-yl dimethylcarbamate), thiometon (S-2-ethylthioethyl O,O-dimethyl phosphorodithioate), BHC (benzene hexachloride), aldrin (1,2,3,4,10,10-hexachloro-1,4a,4,5,8,8a-hexahydro-exo-1,4-endo-5,8-dimethanonaphthalene), fenitrothion (O,O-dimethyl O-4-nitro-m-tolyl phosphorothioate), omethoate (O,O-dimethyl S-methylcarbamoylmethyl phosphorothioate), pirimiphos-methyl (0,2-dimethylamino-6-methylpyrimidin-4-yl O,O-dimethyl phosphorothioate) and DDT (1,1,1-trichloro-2,2-di[chlorophenyl]ethane).

The ratio of the present compound to the other pesticide or plant growth regulant may vary over a wide range according to the particular compounds involved and the intended use. In general the ratio of present compound to other pesticide or plant growth regulant lies in the range 1:0.1 to 1:15.

The present compounds may be in admixture with nonphytotoxic oils, e.g. Agri-Oil Plus, Sun Oil 11E or Fyzol E.

The compounds may be in admixture with fertilizers.

The present compounds are usually employed for herbicidal purposes at a rate of from 0.5 to 8 kg per hectare, for example 1 to 4 kg per hectare.

The present compounds may be applied to plants, the soil, land or aquatic areas.

The compounds of formula I may in certain instances exist in tautomeric or isomeric forms, e.g. those compounds of formula I in which $XR^3$ and $ZR^4$ together form carbonyl oxygen may exist in the enolic form of formula VIII,

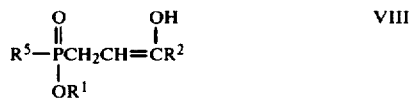

in which $R^1$, $R^2$ and $R^5$ are as defined above.

The enols of formula VII may form derivatives of the enolic —OH.

The present compounds show advantages in the form of different and more active herbicidal properties, ease of synthesis, toxicity, and/or ease of formulation etc as compared to related known compounds.

The invention is further described, though only by way of illustration, in the following Examples.

EXAMPLE 1

4-(Hydroxymethylphosphinyl)-2-oxobutanoic acid (a) Sodium (1.4 g) was dissolved in excess ethanol and the ethanol was distilled off and replaced by toluene (20 ml). The stirred mixture was cooled and dry ether (60 ml) was added followed by diethyl oxalate (8.8 g) and ethyl 3-(ethoxymethylphosphinyl)propanoate (12.6 g). The mixture warmed slightly, was cooled briefly in an ice bath and then stirred at ambient temperature for 24 hours. The resulting solution was extracted with water ($4\times30$ ml) and the combined aqueous extracts were washed with ether and acidified with conc. hydrochloric acid (120 ml). The acidic solution was refluxed for 8 hours, cooled, evaporated in vacuo and most of the acid removed by adding water and re-evaporating. The resulting material was triturated with acetone, sodium chloride was filtered off and the filtrate evaporated to give a brown oil which, on trituration with ether and prolonged scratching gave a solid (8.8 g). This solid was recrystallised from acetone/ether to give colourless crystals, m.p. 105°–7° C. (softens 104° C.) (3.0 g). Further material can be obtained by evaporation of the liquors.

Analysis: Found: C, 33.4; H, 5.0. $C_5H_9O_5P$ requires: C, 33.34; H, 5.04%.

(b) A suspension of sodium ethoxide in toluene (50 ml) was prepared as in (a) above and to this was added diethyl oxalate (10.9 g) and a solution of ethyl 3-(hydroxymethylphosphinyl)propanoate (13.5 g) in toluene (75 ml). The mixture was stirred for 16 hours then extracted with water ($4\times60$ ml). The extract was acidified with conc. hydrochloric acid (200 ml) and the acid solution refluxed for 2.5 hours. The crude product (8.8 g) was isolated as in part (a) and triturated with acetone to give the desired product (5.2 g).

EXAMPLE 2

Disodium salt of compound of Example 1

The compound of Example 1 (3.5 g) was dissolved in water (25 ml) and 2N aqueous sodium hydroxide was added to bring the pH to 7.0. The resulting solution was evaporated in vacuo and the residue triturated with ethanol to give the disodium salt, which was filtered off, washed with ethanol and dried in vacuo. The product was deliquescent, mp 300° C.

Analysis: Found: C, 25.2; H, 4.1. $C_5H_7Na_2O_5P \cdot H_2O$ requires: C, 24.81; H, 3.75%.

EXAMPLE 3 to 10

By the procedure of Example 2 the compound of Example I was treated with two equivalents of, for example, ammonia (or an organic amine) to generate the corresponding diammonium (or bisamine) salt. Alternatively one equivalent of for example, sodium hydroxide, ammonia or an organic amide can be used to prepare a monosodium, monoammonium or monoamine salt. Furthermore, one equivalent of, for example sodium hydroxide, followed by a second equivalent of, for example an organic amine, can be used to prepare mixed salts.

By these methods the following salts were prepared.

EXAMPLE 3

Diammonium salt

A slightly deliquescent solid, mp 135°–136° C.

Analysis: Found: C, 27.62; H, 6.91. $C_5H_{15}N_2O_5P$ requires: C, 28.04; H, 7.06%.

EXAMPLE 4

Bis(isopropylamine) salt

Colourless solid, mp 128°–130° C.

Analysis: Found: C, 44.1; H, 9.1. $C_{11}H_{27}N_2O_5P$ requires: C, 44.09; H, 9.12%.

EXAMPLE 5

Bis(dicyclohexylamine) salt

Colourless solid, mp 76° C.
Analysis: Found: C, 64.44; H, 10.16. $C_{29}H_{55}N_2O_5P$ requires: C, 64.17; H, 10.22%.

EXAMPLE 6

Bis(decylamine) salt

Colourless deliquescent solid, mp 199°–200° C.
Analysis: Found: C, 61.17; H, 11.63. $C_{25}H_{55}N_2O_5P$ requires: C, 60.7; H, 11.21%.

EXAMPLE 7

Dipotassium salt

Colourless deliquescent solid of undefined melting point.
Analysis: Found: C, 23.0; H, 3.2. $C_5H_7K_2O_5P$ requires: C, 23.43; H, 2.75%.

EXAMPLE 8

Monosodium salt

Colourless deliquescent solid of undefined melting point.
Analysis: Found: C, 29.6; H, 4.3. $C_5H_8NaO_5P$ requires: C, 29.72; H, 3.99%.

EXAMPLE 9

Sodium Isopropylamine salt

Off-white deliquescent solid of undefined melting point.
Analysis: Found: C, 36.45; H, 6.7; N, 5.0. $C_8H_{17}NNaO_5P$ requires: C, 36.79; H, 6.56; N, 5.36%.

EXAMPLE 10

Mono(isopropylamine) salt

An extremely deliquescent viscous gum which was shown to be pure by its n.m.r. spectrum.

EXAMPLE 11

Ethyl 4-(hydroxymethylphosphinyl)-2-oxobutanoate

A solution of the compound of Example 1 (9.0 g) in ethanol (17.5 ml) and toluene (10 ml) containing a catalytic amount of p-toluene sulphonic acid was boiled under reflux under a Dean and Stark trap. After 3 hours the liquid in the trap was removed, boiling continued for one hour, further liquid removed from the trap and finally boiling continued for a further hour.

The cooled solution was evaporated to dryness and the residue treated with a toluene/dichloromethane mixture (4:1). Insoluble material was filtered off and the filtrate evaporated to dryness in vacuo to give a pale yellow oil (9.2 g). The n.m.r. spectrum was in agreement with the proposed structure.

Analysis: Found: C, 35.45; H, 7.0. $C_7H_{13}O_5P$ 1.5 $H_2O$ requires: C, 35.7; H, 6.8%.

By essentially the same procedure, using benzene as solvent and with removal of water, the esters of Example 12 and 13 prepared.

EXAMPLE 12

The monoisopropyl ester

Colourless oil. The n.m.r. and i.r. spectra showed the presence of the required compound.

EXAMPLE 13

The monoallyl ester

Isolated as the cyclohexylamine salt, mp 120°–125° C. The n.m.r. and i.r. spectra showed the presence of the required compound.

EXAMPLE 14

Ethyl 4-(ethoxymethylphosphinyl)-2-oxobutanoate

The compound of Example 1 (2.0 g) was dissolved with heating in acetonitrile (100 ml). To this was added triethylamine (2.26 g) and the solution was boiled under reflux for 15 minutes then cooled. Ethyl bromide (10 ml) was added and the stirred solution was boiled under reflux for 6 hours then cooled and evaporated to dryness in vacuo, and the residue extracted with ether. The extracts were combined and evaporated in vacuo to give the diester as a yellow oil (1.1 g). The n.m.r. spectrum was consistent with the proposed structure.

Analysis: Found: C, 45.3; H, 6.84. $C_9H_{17}O_5P$ requires: C, 45.76; H, 7.25%.

EXAMPLE 15

2-[2-(Hydroxymethylphosphinyl)ethyl]thiazolidine-2-carboxylic acid, disodium salt 2-Mercaptoethylamine hydrochloride (0.98 g) was added to a solution of sodium hydroxide (0.35 g) in ethanol (10 ml). Sodium chloride was filtered off and to the resulting solution of the free amine was added a solution of sodium hydroxide (0.7 g) in ethanol (10 ml) followed by 4-(hydroxymethylphosphinyl)-2-oxobutanoic acid (1.56 g). A precipitate appeared immediately and the mixture was boiled under reflux for one hour, cooled, and diluted with ether. The crude thiazolidine was filtered off and purified by dissolution in methanol and reprecipitation with ether, yield 2.0 g, mp 300° C.

Analysis: Found: C, 29.18; H, 4.46; N, 4.52. $C_7H_{12}NNa_2O_4PS$ requires: C, 29.69; H, 4.27; N, 4.95%.

EXAMPLE 16

2,2-Diethoxy-4-(hydroxymethylphosphinyl)butanoic acid, disodium salt

The compound of Example 1 (5.0 g) was dissolved in ethanol (200 ml). 4A molecular sieve (30 g) was added, and the mixture was boiled under reflux with stirring for two hours. The solution was then decanted onto a further portion of molecular sieve (20 g) and boiled under reflux for two hours as before. The mixture was cooled, the solids filtered off and the filtrate diluted with icewater (20 ml) then taken to pH 7.0 with 2N sodium hydroxide. The resulting solution was evaporated in vacuo giving a colourless solid. This was triturated with ethanol, filtered off, washed with ethanol and ether and dried (5.3 g). The crude product was then stirred briefly with hot ethanol (200 ml) and the insoluble material was filtered off, washed with a little ethanol, then ether, and dried in vacuo. This gave the desired product as a deliquescent solid (2.1 g), decomp 220° C. The n.m.r. and i.r. spectra were in agreement with the proposed structure.

Analysis: Found: C, 30.58; H, 6.13. $C_9H_{17}Na_2O_6P.3H_2O$ requires: C, 30.68; H, 6.53%.

EXAMPLE 17

2,2-Di-n-propoxy-4-(hydroxymethylphosphinyl)-butanoic acid, disodium salt

By the procedure of Example 16 the compound of Example 1 (5.0 g) was treated with n-propanol at 80°–85° C. The crude product (3.2 g) was purified by the procedure of Example 16 giving a deliquescent solid, the n.m.r. and i.r. spectra of which showed the presence of the title compound.

EXAMPLE 18

Ethyl 4-(ethoxymethylphosphinyl)-2,2-di-(ethylthio)-butanoate

A mixture of ethyl o-nitrophenylethyldisulphide (22.3g) and ethyl 4-(ethoxymethylphoshinyl)butanoate (10.0g.) was dissolved in tetrahydrofuran (250ml) and sodium hydride (2.8g; 80% dispersion in oil) was added with stirring. After the initial reaction had subsided the reaction mixture was boiled under reflux for 6 hours, cooled, and evaporated in vacuo. The residue was treated with ether, insoluble material filtered off and the filtrate evaporated in vacuo to give the crude product as an oil. This oil was purified by chromatography on silica gel. After elution of impurities with light petroleum (b.p. 60°–80° C.)/ethyl acetate (9:1) elution with methanol gave the desired product as an orange oil (1.6g).

Analysis: Found: C 45.99; H 7.93%. $C_{13}H_{27}O_4PS_2$ requires: C 45.59; H 7.95%.

EXAMPLE 19

Semicarbazone of 4-(hydroxymethylphosphinyl)-2-oxobutanoic acid

The compound of Example 1 (3.0 g) was dissolved in water (20ml) and semicarbazide hydrochloride (2.0 g) was added. The solution was adjusted to pH 12.0 with 2N sodium hydroxide, kept at ambient temperature for 2 hours then acidified with concentrated hydrochloric acid and cooled in ice. The semicarbazone crystallised on cooling and was filtered off, washed with ice-cold water and dried. The crude product (3.1g) was purified by recrystallisation from water, giving colourless needles m.p. 188° C.

Analysis: Found: C 29.98; H 4.77; N 17.32%. $C_6H_{12}N_3O_5P$ requires: C 30.39; H 5.1; N 17.72%.

EXAMPLE 20

Thiosemicarbazone of 4-(hydroxymethylphosphinyl)-2-oxobutanoic acid

The compound of Example 1 (2.0 g) was dissolved in water (10 ml) and a solution of thiosemicarbazide (1.34 g) in water (50 ml) was added. The mixture was stirred at ambient temperature for 16 hours and the precipitated thiosemicarbazone was filtered off, washed successively with ice-cold water, ethanol and ether and dried in vacuo to yield 2.9 g of the desired product; m.p. 199°–200° C.

Analysis Found: C 28.73; H 5.0; N 16.23%. $C_6H_{12}N_3O_4PS$ requires: C 28.46; H 4.78; N 16.6%.

EXAMPLE 21

2-Cyano-2-hydroxy-4-(hydroxymethylphosphinyl)-butanoic acid, dipotassium salt

The compound of Example 1 (3.6 g) was added in small portions to an ice-cooled stirred solution of potassium cyanide (3.0 g) in water (20 ml). The pH of the solution was adjusted to 6.0 with acetic acid and the solution was stirred overnight at ambient temperature. Glacial acetic acid (15 ml) was added and the solution was evaporated to dryness in vacuo.

The oily residue was triturated with ether (2×50mm). The insoluble residue was then triturated with ethanol (2×50ml) to give the cyanohydrin as a deliquescent solid which was filtered off, washed with ethanol and ether and finally dried in vacuo, to yield 0.9 g of the desired product; m.p. 88°–90° C. (decomp.).

The n.m.r. and i.r. spectra were in agreement with the required product.

EXAMPLE 22

2-Hydroxy-4-(hydroxymethylphosphinyl)-2-sulphobutanoic acid, trisodium salt

A solution of the compound of Example 1 (1.85 g) in water (10 ml) containing sodium hydroxide (1.23 g) was saturated with sulphur dioxide. The stirred solution was left for one hour at ambient temperature maintaining a slow stream of sulphur dioxide. Excess sulphur dioxide was removed in vacuo and the solution was diluted with ethanol (100 ml). A sticky solide precipitated. The liquid was decanted off and the residue was dissolved in methanol. Dilution with ether gave the bisulphite adduct as a solid which was filtered off, washed with ether and dried in vacuo. The i.r. and n.m.r. spectra were in agreement with the required compound.

Analysis: Found: C 18.45; H 2.95%. $C_5H_8Na_3O_8PS$ requires: C 18.3; H 2.46%.

EXAMPLE 23

2,4-Dinitrophenylhydrazone of 4-(hydroxymethylphosphinyl)-2-oxobutanoic acid

The compound of Example 2 (2.25 g) was suspended in ethanol (200 ml) and 2,4-dinitrophenylhydrazine (2.0 g) was added. The mixture was heated under reflux, with stirring, until a clear solution was obtained. This solution was cooled, evaporated in vacuo and the residue dissolved in the minimum of water and then acidified with conc. hydrochloric acid. The resulting precipitate was filtered off, washed with water and dried. This product (0.5 g) was recrystallised from aqueous ethanol to give orange crystals of the desired product, m.p. 229° C. (decomp.).

Analysis: Found: C 36.45; H 3.80; N 15.30%. $C_{11}H_{13}N_4O_8P$ requires: C 36.67; H 3.64; N 15.55%.

EXAMPLE 24

Ethyl 4-(ethoxymethylphosphinyl)-2-oximinobutanoate (a) Diethyl [(2-ethoxymethylphosphinyl)ethyl]malonate Sodium hydride (80% dispersion in oil; 5.3g) was added in small portions to a solution of diethyl malonate (28.2 g) in dry toluene (500 ml). The resulting slurry was boiled under reflux with stirring for 30 min. then a solution of ethyl (2-bromoethyl)methyl phosphinate (37.9 g) in toluene (50 ml) was added dropwise over 5 min. The mixture was then boiled gently under reflux for 16 hours, sodium chloride was filtered off and the filtrate evaporated to give an orange oil. This was washed with light petroleum (b.p. 40°-60° C.) to give diethyl [(2-ethoxymethylphosphinyl)ethyl]malonate (41.6g) as a yellow-orange oil.

Analysis: Found: C 48.55; H 7.71% $C_{12}H_{23}O_6P$ requires: C48.87; 7.88%

(b) Ethyl 4-(ethoxymethylphosphinyl)-2-oximinobutanoate

To a solution of the product of step (a) (32.2 g) in ethanol (90 ml) cooled to −10° C. was added ethyl nitrite (18 ml) followed by a solution of sodium ethoxide (from sodium (2.65 g) in ethanol (90 ml)), added dropwise over 90 min. The reaction mixture was then stirred at −10° C. for 16 hours evaporated in vacuo and the residue was dissolved in ethanol (150 ml) and acidified to pH 4.0 by the addition of conc. hydrochloric acid. The resulting solution was evaporated in vacuo and the residue treated with a mixture of ether and ethanol (10:1; 150 ml). Sodium chloride was filtered off and the filtrate evaporated in vacuo to give the oxime as a red oil (23.4 g). The n.m.r. spectrum supported the required structure.

EXAMPLE 25

Ammonium salt of 4-(hydroxymethylphosphinyl)-2-oxobutanamide

A solution of isopropyl 2-oxo-4-(hydroxymethylphosphinyl)butanoate (3.0 g) in isopropanol (10 ml) was added to a saturated solution of ammonia in isopropanol (50 ml). The solution was stirred at room temperature for 18 hours during which time a white solid precipitated. This was filtered off, washed with ether and dried in vacuo over anhydrous calcium chloride. Yield = 2.6 g. The product decomposed above 135° C.

The i.r. and n.m.r. spectra were in agreement with the structure of the required compound.

EXAMPLE 26

Diethylamine salt of N,N-diethyl-4-(hydroxymethylphosphinyl)-2-oxobutanamide

A solution of isopropyl 2-oxo-4-(hydroxymethylphosphinyl) butanoate (3.0 g) in isopropanol (50 ml) containing diethylamine (10 ml) was refluxed for 18 hours. The solvent was evaporated in vacuo (finally at 0.1 mm Hg) to leave a thick light-brown oil which failed to solidify on standing. Yield = 4.1 g.

The i.r. and n.m.r. spectra of the product were in agreement with the structure of the required compound.

EXAMPLE 27

2-Acetoxy-4(hydroxymethylphosphinyl)-2-butenoic acid

A solution of 2-oxo-4-(hydroxyphosphinylmethyl)butanoic acid (1.0 g) in acetic anhydride (10 ml) was refluxed for one hour. The solvent was evaporated in vacuo (finally at 0.1 mm Hg) to leave a thick pale brown oil (1.2 g).

This was shown by its n.m.r. and i.r. spectra to be the required enol acetate.

EXAMPLE 28

2-Acetamido-4-(hydroxymethylphosphinyl)-2-butenoic acid

A finely divided mixture of 2-oxo-4-(hydroxymethylphosphinyl)butanoic acid (1.80 g, 10 mmol) and acetamide (1.18 g, 20 mmol) were heated at 100° for 5 hours at 20 mm Hg. The mixture melted with evolution of water vapour. The final product was a yellow glass-like solid which was evacuated at 0.1 mm Hg at 100° for one hour to remove excess acetamide.

An n.m.r. spectrum of the material showed that the required product had been formed.

EXAMPLE 29

Aniline salt of isopropyl 2-anilino-4-(hydroxymethylphosphinyl)-2-butenoate

The product of Example 12 (2.22 g, 10 mmol) was dissolved in benzene (60 ml) and to the solution was added aniline (1.86 g, 20mmol). The solution was refluxed under a Dean and Stark apparatus with removal of water. When the theoretical amount of water had distilled off the resulting yellow solution was evaporated in vacuo to give the crude product as a yellow viscous gum. The n.m.r. spectrum showed the presence of the required product.

EXAMPLE 30

Dipotassium salt of 4-(hydroxymethylphosphinyl)-2-oximinobutenoate

Finely ground hydroxylamine hydrochloride was added in small portions to a stirred solution of potassium hydroxide (3.36 g, 60mmol) in ethanol (60 ml) containing a trace of phenolphthalein as indicator. As soon as the purple colouration disappeared the mixture was quickly filtered and the filtrate was added to a solution of the compound of Example 7 (5.12 g, 20 mmol) in water (50 ml) and the resulting solution was warmed on a water bath for 2 hours.

The solution was evaporated to dryness to give a residue which was recrystallised from methanol to give the required product as a colourless solid (0.61 g), mp 137°-8° (dec). The i.r. and n.m.r. spectra were in agreement with the proposed structure.

EXAMPLE A

Seeds of Peas, Mustard, Linseed, Ryegrass, Sugarbeet, Oats and French beans were sown in anodised aluminium pans, 19 cm long × 95. cm wide × 5 cm deep containing John Innes I potting compost. They were then watered and placed in a controlled environment room (22° C.; 65–85% RH; 14 hours artificial illumination at 1200 foot candles). Fourteen days after sowing the seedlings received a foliar spray of the test compound formulated as an aqueous solution together with 1000 ppm of the wetting agent Synperonic NX.

The concentrations of active ingredient and volume of application were adjusted so as to be equivalent to a rate of 2.8 or 0.7 kg/ha in 450 liters per hectare.

After seven days growth in a controlled environment room the plants were visually assessed for any herbicial or growth regulant response. All differences from the untreated control were scored according to a herbicidal index were 0 = no effect and 100 = complete kill.

The results are summarised in the Table below.

EXAMPE B

Seeds of various monocotyledon species, listed below, were sown in anodised aluminium pans 19 cm long×9.5 cm wide×5.0 cm deep, containing John Innes I potting compost. They were then watered and placed in a controlled environment room (22° C.; 65–86% RH; 14 hours artifical illumination at 1600 foot candles). Fourteen days after sowing the seedling were given a foliar spray of the compounds under test formulated as an aqueous solution together with 2000 ppm of the wetting agent Synperonic NX. The dosage rate was adjusted to be 0.7 or 0.175 kg active ingredient in 450 liters per hectare.

After a further 14 days in the controlled environment room the plants were visually assessed for any growth regulatory or herticidal effect. All differences from an untreated control were scored on a scale 0–100 where 0 signifies no effect and 100 signifies complete suppression.

The results are summarised in the Table below.

EXAMPLE C

Seeds of the plant species listed in the Table were sown in John Innes I potting compost in anodised aluminium pans, 19 cm long×9.5 cm wide×5.0 cm deep, and placed in a controlled environment room (22° C.; 65–85% RH; 14 hours per day artificial illumination, at 17,000 lux). When all the species had at least 2 fully expanded true leaves, the plants received a foliar spray of the test compound formulated as an aqueous solution together with 1 g of the ethylene oxide-nonyl phenol condensate wetting agent Synperonic NX per liter. One pan of each species received the equivalent of 0.175 kg of the compound under test in 450 liters per hectare and was returned to the controlled environment room. Fourteen days after treatment, the plants were visually assessed for any herbicidal or growth regulant effects. All differences from an untreated control were scored according to an index where 0=no effect and 100=complete kill. The results are shown in the Table below.

TABLE

| Compound of Example No | Procedure of Example A Dosage kg/ha | | | | | | | | | | | |
|---|---|---|---|---|---|---|---|---|---|---|---|---|
| | 2.8 | | | | | | 0.7 | | | | | |
| | Peas | Mustard | Linseed | Ryegrass | Oats | Sugarbeet | Peas | Mustard | Linseed | Ryegrass | Oats | Sugarbeet |
| 1 | 90 | 100 | 100 | 100 | 100 | 100 | 70 | 100 | 50 | 80 | 90 | 100 |
| 2 | 80 | 100 | 100 | 100 | 80 | 100 | 70 | 95 | 80 | 85 | 40 | 95 |
| 3 | 100 | 100 | 100 | 95 | 90 | 100 | 75 | 100 | 90 | 95 | 35 | 100 |
| 4 | 95 | 100 | 95 | 100 | 95 | 100 | 70 | 100 | 100 | 100 | 70 | 100 |
| 5 | 95 | 100 | 100 | 100 | 70 | 100 | 65 | 100 | 95 | 90 | 30 | 100 |
| 11 | 75 | 100 | 100 | 100 | 85 | 100 | 60 | 100 | 100 | 85 | 30 | 100 |
| 12 | 40 | 100 | 100 | 85 | 50 | 100 | | | | | | |
| 15 | 85 | 100 | 100 | 85 | 80 | 100 | 40 | 95 | 50 | 90 | 20 | 95 |
| 16 | 50 | 100 | 30 | 85 | 20 | 90 | 25 | 90 | 10 | 40 | 0 | 55 |
| 17 | 85 | 100 | 100 | 100 | 95 | 100 | 20 | 100 | 20 | 40 | 5 | 95 |
| 19 | 80 | 100 | 100 | 100 | 40 | 100 | 5 | 95 | 3 | 55 | 3 | 15 |
| 20 | 90 | 100 | 100 | 100 | 55 | 100 | 35 | 100 | 85 | 100 | 30 | 100 |
| 21 | 100 | 100 | 100 | 100 | 100 | 100 | 85 | 100 | 100 | 100 | 100 | 100 |
| 22 | 90 | 100 | 95 | 95 | 80 | 100 | 80 | 100 | 95 | 90 | 35 | 100 |

| Compound of Example No | Procedure of Example B Dosage kg/ha | | | | | | | | | | | | |
|---|---|---|---|---|---|---|---|---|---|---|---|---|---|
| | 0.7 | | | | | | | 0.175 | | | | | |
| | Wheat | Barley | Wild Oats | Blackgrass | Barnyardgrass | Crabgrass | Johnsongrass | Wheat | Barley | Wild Oats | Blackgrass | Barnyardgrass | Crabgrass |
| 1 | 100 | 70 | 75 | 65 | 95 | 100 | 100 | 65 | 30 | 50 | 50 | 85 | 100 |
| 2 | 90 | 40 | 50 | 75 | 65 | 100 | 100 | 60 | 30 | 20 | 30 | 45 | 100 |
| 3 | 65 | 30 | 50 | 85 | 35 | 100 | 90 | 25 | 25 | 20 | 30 | 20 | 100 |
| 4 | 100 | 65 | 75 | 100 | 40 | 100 | 100 | 40 | 25 | 25 | 25 | 35 | 100 |
| 5 | 100 | 35 | 65 | 85 | 25 | 100 | 95 | 35 | 20 | 15 | 25 | 30 | 100 |
| 11 | 75 | 35 | 50 | 85 | 70 | 100 | 100 | 25 | 5 | 15 | 20 | 30 | 100 |
| 12 | | | | | | | | | | | | | |
| 15 | 95 | 35 | 35 | 75 | 45 | 100 | 100 | 15 | 25 | 15 | 5 | 10 | 100 |
| 16 | | | | | | | | 25 | 20 | 3 | 5 | 5 | 85 |
| 17 | | | | | | | | 15 | 20 | 3 | 20 | 10 | 100 |
| 19 | | | | | | | | 10 | 10 | 0 | 5 | 5 | 80 |
| 20 | | | | | | | | 20 | 20 | 15 | 5 | 15 | 100 |
| 21 | 70 | 65 | 75 | 75 | 75 | 100 | 100 | | | | | | |
| 22 | 85 | 55 | 65 | 75 | 90 | 100 | 100 | | | | | | |

| Compound of Example No | Procedure of Example C Dosage kg/ha 0.175 | | | | | | | | |
|---|---|---|---|---|---|---|---|---|---|
| | Johnsongrass | Ryegrass | Chickweed | Maywed | Cleavors | Pale Persicaria | Fathen | Corn Marigold | Pigweed |
| 1 | 100 | 70 | 90 | 100 | 25 | 35 | 100 | 100 | 70 |
| 2 | 80 | 25 | 75 | 100 | 75 | 75 | 95 | 100 | 100 |
| 3 | 75 | 15 | 50 | 100 | 50 | 75 | 65 | 100 | 90 |
| 4 | 85 | 25 | 65 | 100 | 65 | 85 | 80 | 100 | 95 |
| 5 | 75 | 30 | 60 | 100 | 65 | 85 | 80 | 100 | 100 |
| 11 | 75 | 15 | 65 | 75 | 30 | 50 | 100 | 100 | 95 |
| 12 | | | | | | | | | |
| 15 | 55 | 10 | 30 | 60 | 30 | 30 | 40 | 90 | 90 |
| 16 | 20 | 5 | 5 | 35 | 20 | 20 | 45 | 35 | 25 |
| 17 | 40 | 20 | 10 | 100 | 15 | 35 | 75 | 100 | 45 |

TABLE-continued

| 19 | 20 | 5 | 25 | 25 | 30 | 20 | 85 | 90  | 50 |
| -- | -- | - | -- | -- | -- | -- | -- | --- | -- |
| 20 | 55 | 5 | 15 | 35 | 15 | 20 | 90 | 100 | 90 |
| 21 |    |   |    |    |    |    |    |     |    |
| 22 |    |   |    |    |    |    |    |     |    |

EXAMPLE D

Plots of potatoes and peas of 3 m×2 m size were treated with the compound of Example 1, made up in distilled water (1 liter) with 'Tween' 20 wetting agent added at 0.2% spray volume. The compound was applied at rates of 1 and 3 kg ai/ha, or 5 and 15 g technical material in 1 liter water, equivalent to a volume application rate of 200 l/ha.

The solution was applied by knapsack sprayer with a 2 m wide boom. There were two replicates per treatment.

At the time of application the potatoes and peas were just prior to harvest stage of growth.

The results are given below:

| rate kg ai/ha | Potatoes | Peas |
| ------------- | -------- | ---- |
| 1             | 97       | 90   |
| 3             | 97       | 95   |

On a scale 0 no effect–100 no visible green leaf (100% kill/desiccation).

We claim:

1. A compound of the formula:

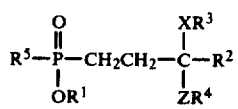

wherein $R^5$ is methyl or halomethyl;

$R^1$ is hydrogen, a cation or alkyl;

$R^2$ is carboxyl or a salt, ester of amide thereof;

X and Z, which may be the same or different, are each —O—, —S— or —NR$^7$— wherein $R^7$ is hydrogen or alkyl;

$R^3$ and $R^4$, which may be the same or different, are each alkyl or together form an alkylene chain; or one of XR$^3$ and ZR$^4$ is —OH and the other is —CN or —SO$_3^\ominus$ cation; or XR$^3$ and ZR$^4$ together form carbonyl oxygen, or a hydrazone, oxime, semicarbazone or thiosemicarbazone derivative thereof.

2. A compound according to claim 1 wherein when $R^1$ represents a cation or when —XR$^3$ or —ZR$^4$ represents —SO$_3^\ominus$ cation, the cation is an alkali metal, an alkaline earth metal, an ammonium, or a protonated primary-, secondary- or tertiary-, or a quaternary-ammonium cation.

3. A compound according to claim 1 wherein $R^1$ is selected from hydrogen, ethyl or propyl.

4. A compound according to claim 1 wherein —XR$^3$ and —ZR$^4$, when they are separate, each contain up to and including 10 carbon atoms.

5. A compound according to claim 1 wherein $R^7$ is alkyl containing up to 10 carbon atoms.

6. A compound according to claim 1 wherein $R^5$ is methyl; $R^2$ is —CONRaRb in which Ra and Rb independently represent hydrogen or alkyl C 1 to 6, or $R^2$ is —COOR$^6$ in which $R^6$ is hydrogen, a cation, alkenyl C 2 to 6, benzyl, or alkyl C 1 to 6 optionally substituted by —CN; $R^1$ is hydrogen, a cation or alkyl C 1 to 6 optionally substituted by —CN; —XR$^3$ and —ZR$^4$ together form carbonyl oxygen, =N—NHCONH$_2$, =N—NHCSNH$_2$, =N—NH(2,4-dinitrophenyl), =NOH or a chain —SCH$_2$CH$_2$NH—, or represent the pairs of groups —OH and —CN, or —OH and —SO$_3^\ominus$.

7. Compounds according to claim 1 having the structures:

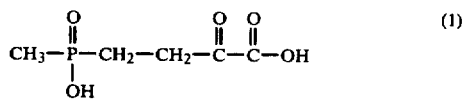

(2) disodium salt of compound (1)
(3) diammonium salt of compound (1)
(4) bis(isopropylamine) salt of compound (1)
(5) bis(dicyclohexylamine) salt of compound (1)
(6) bis(decylamine) salt of compound (1)
(7) dipotassium salt of compound (1)
(8) monosodium salt of compound (1)
(9) sodium, isopropylamine salt of compound (1)
(10) mono(isopropylamine) salt of compound (1)

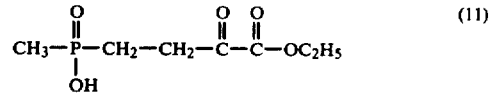

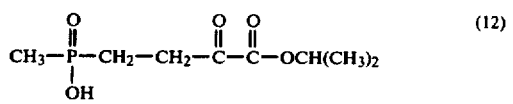

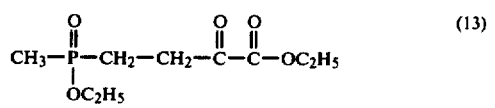

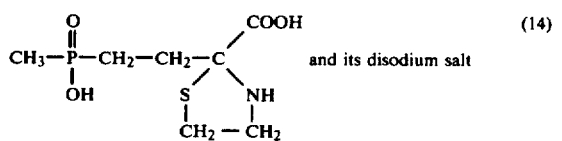

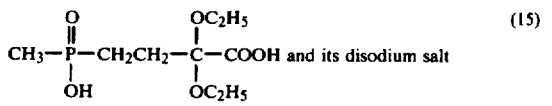

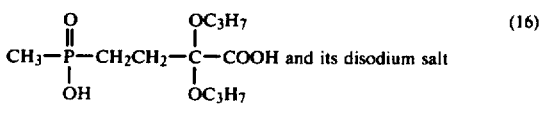

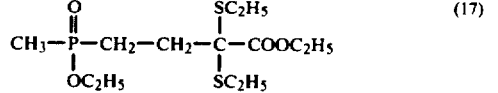

-continued
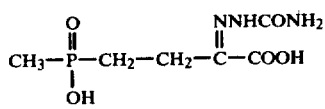 (18)
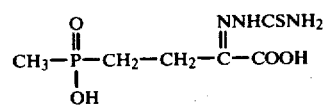 (19)
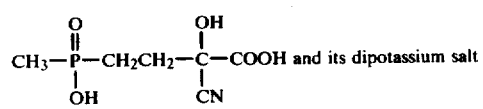 (20)
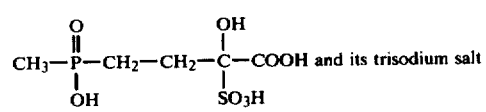 (21)
-continued
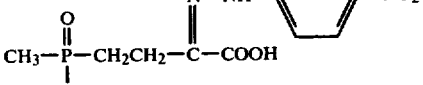 (22)
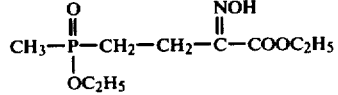 (23)
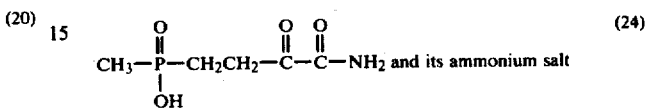 (24)
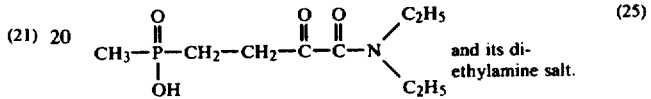 (25)
* * * * *